(12) United States Patent
Twomey

(10) Patent No.: US 8,945,175 B2
(45) Date of Patent: Feb. 3, 2015

(54) LATCH MECHANISM FOR SURGICAL INSTRUMENTS

(75) Inventor: John R. Twomey, Superior, CO (US)

(73) Assignee: Covidien LP, Mansfield, MA (US)

( * ) Notice: Subject to any disclaimer, the term of this patent is extended or adjusted under 35 U.S.C. 154(b) by 403 days.

(21) Appl. No.: 13/006,538

(22) Filed: Jan. 14, 2011

(65) Prior Publication Data

US 2012/0184989 A1    Jul. 19, 2012

(51) Int. Cl.
*A61B 17/00*    (2006.01)
*A61B 18/14*    (2006.01)
*A61B 17/29*    (2006.01)
*A61B 18/00*    (2006.01)

(52) U.S. Cl.
CPC ......... *A61B 18/1445* (2013.01); *A61B 17/2909* (2013.01); *A61B 2017/00734* (2013.01); *A61B 2017/2946* (2013.01); *A61B 2018/0091* (2013.01)
USPC ............................ 606/206; 606/208; 600/106

(58) Field of Classification Search
CPC ........... A61B 17/2909; A61B 18/1445; A61B 2018/0091; A61B 2017/2946; A61B 2017/00734; A61B 2017/2913; A61B 2017/2915; A61B 2017/2916; A61B 2017/2919; A61B 2017/2933; A61B 2017/2934
USPC ................. 27/60; 81/407–412; 30/183–185; 294/101, 104; 204/106, 116; 227/178.1, 197.1
See application file for complete search history.

(56) References Cited

U.S. PATENT DOCUMENTS

| D249,549 | S | 9/1978 | Pike |
| D263,020 | S | 2/1982 | Rau, III |
| D295,893 | S | 5/1988 | Sharkany et al. |
| D295,894 | S | 5/1988 | Sharkany et al. |
| D298,353 | S | 11/1988 | Manno |
| D299,413 | S | 1/1989 | DeCarolis |
| 5,084,057 | A | 1/1992 | Green et al. |
| 5,211,655 | A | 5/1993 | Hasson |
| D343,453 | S | 1/1994 | Noda |

(Continued)

FOREIGN PATENT DOCUMENTS

| DE | 2415263 | 10/1975 |
| DE | 2514501 | 10/1976 |

(Continued)

OTHER PUBLICATIONS

U.S. Appl. No. 08/926,869, filed Sep. 10, 1997, James G. Chandler.

(Continued)

*Primary Examiner* — Katherine Dowe
*Assistant Examiner* — Sidharth Kapoor

(57) ABSTRACT

A latch mechanism for a surgical instrument includes a lever moveable from an initial position to an actuated position for moving an end effector assembly from a first to a second state. A pin extends from the lever. A cantilever spring is operably engaged to the housing of the instrument. A pin track member is operably engaged to the cantilever spring at a free end thereof. The pin track member is configured to permit translation of the pin therealong between a first position corresponding to the initial position of the lever and a second position corresponding to the actuated position of the lever. The pin is configured to translate from the first to the second position along a first path and from the second position back to the first position along a second path and is configured to be releasably retained in the second position.

18 Claims, 6 Drawing Sheets

(56) References Cited

U.S. PATENT DOCUMENTS

| | | |
|---|---|---|
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,564,615 A | 10/1996 | Bishop et al. |
| D384,413 S | 9/1997 | Zlock et al. |
| 5,725,536 A | 3/1998 | Oberlin et al. |
| D402,028 S | 12/1998 | Grimm et al. |
| 5,893,863 A | 4/1999 | Yoon |
| 5,935,126 A | 8/1999 | Riza |
| D416,089 S | 11/1999 | Barton et al. |
| D424,694 S | 5/2000 | Tetzlaff et al. |
| D425,201 S | 5/2000 | Tetzlaff et al. |
| 6,179,834 B1 | 1/2001 | Buysse et al. |
| D449,886 S | 10/2001 | Tetzlaff et al. |
| D454,951 S | 3/2002 | Bon |
| D457,958 S | 5/2002 | Dycus et al. |
| D457,959 S | 5/2002 | Tetzlaff et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,628,791 B2 | 12/2009 | Garrison et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 2002/0013583 A1 | 1/2002 | Camran et al. |
| 2005/0033278 A1 | 2/2005 | McClurken et al. |
| 2006/0190035 A1 | 8/2006 | Hushka et al. |
| 2006/0287641 A1 | 12/2006 | Perlin |
| 2007/0233019 A1* | 10/2007 | Forsell ............... 604/288.03 |
| 2009/0312603 A1* | 12/2009 | Lam et al. ............... 600/106 |
| 2011/0264093 A1* | 10/2011 | Schall ............... 606/52 |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 19738457 | 1/2009 |
| DE | 10 2008 018406 | 7/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 6-285078 | 10/1994 |
| JP | 6-511401 | 12/1994 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| JP | 2001-190564 | 7/2001 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, Jun. 9, 2000, Thomas P. Ryan.
U.S. Appl. No. 12/336,970, filed Dec. 17, 2008, Paul R. Sremeich.
U.S. Appl. No. 12/576,380, filed Oct. 9, 2009, Wayne Siebrecht.
U.S. Appl. No. 12/607,191, Oct. 28, 2009, William H. Nau Jr.
U.S. Appl. No. 12/619,100, filed Nov. 16, 2009, Jennifer S. Harper.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.

(56) References Cited

OTHER PUBLICATIONS

U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/004,984, filed Jan. 12, 2011, David M. Garrison.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/048,679, filed Mar. 15, 2011, Paul Guerra.
U.S. Appl. No. 13/075,847, filed Mar. 30, 2011, Gary M. Couture.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.

(56) References Cited

OTHER PUBLICATIONS

E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181969.6 dated Feb. 4, 2011.
Int'l Search Report EP 10 191320.0 dated Feb. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

\* cited by examiner

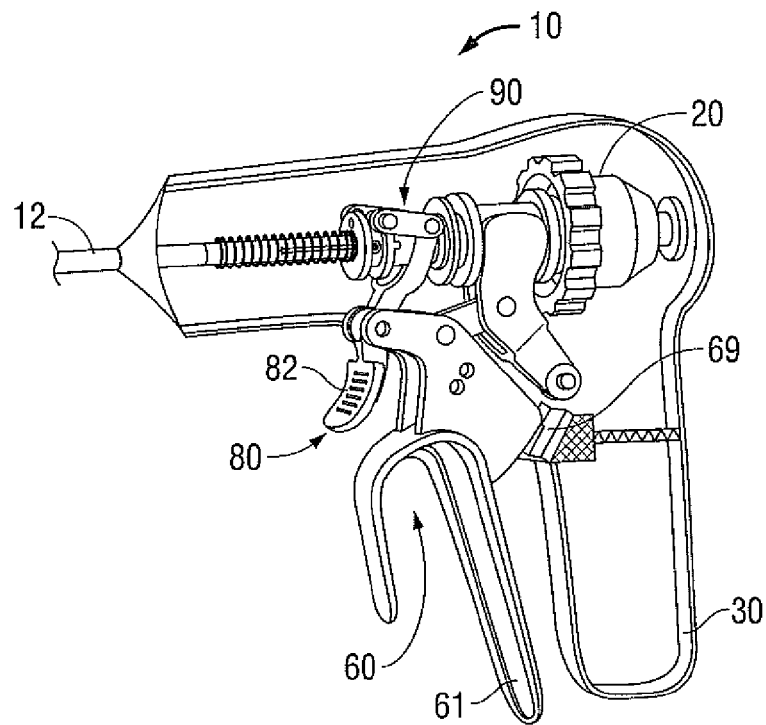
FIG. 7
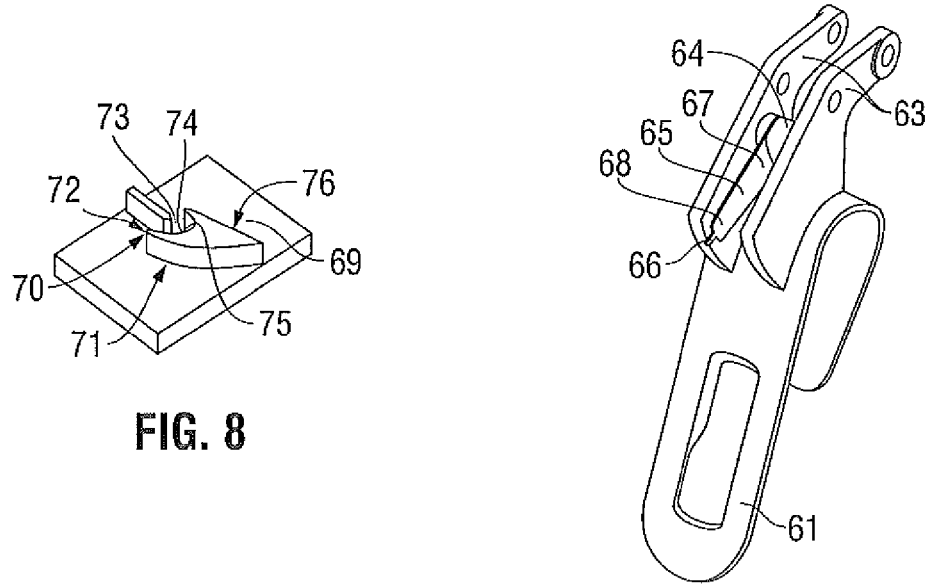
FIG. 8
FIG. 9

LATCH MECHANISM FOR SURGICAL INSTRUMENTS

BACKGROUND

The present disclosure relates to surgical instruments. More particularly, the present disclosure relates to releasable latch mechanisms for use with surgical instruments.

TECHNICAL FIELD

Electrosurgical instruments, e.g., forceps, utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue. Typically, after a vessel or tissue is sealed, the surgeon advances a knife to sever the sealed tissue disposed between the opposing jaw members.

SUMMARY

The present disclosure relates to a latch mechanism for use with a surgical instrument. The latch mechanism includes a lever moveable relative to a housing of the surgical instrument from an initial position to an actuated position for moving an end effector assembly of the surgical instrument from a first state to a second state. A pin extends from the lever and a cantilever spring is operably engaged to the housing of the surgical instrument at a fixed end thereof. A pin track member is operably engaged to the cantilever spring at a free end of the cantilever spring. The pin track member is configured to permit translation of the pin therealong between a first position corresponding to the initial position of the lever and a second position corresponding to the actuated position of the lever. The pin is configured to translate from the first position to the second position along a first path and from the second position back to the first position along a second path different from the first path. The pin is further configured to be releasably retained in the second position upon translation of the pin from the first position to the second position along the first path.

In one embodiment, the cantilever spring is biased toward alignment with a neutral axis defined therein. The cantilever spring is capable of flexing in each of a positive direction and a negative direction relative to the neutral axis to permit translation of the pin along the first and second paths.

In another embodiment, the cantilever spring is configured to deflect in the negative direction relative to the neutral axis to permit translation of the pin from the first position to the second position along the first path. On the other hand, the cantilever spring may be configured to deflect in the positive direction relative to the neutral axis to permit translation of the pin from the second position back to the first position along the second path.

In yet another embodiment, the cantilever spring is substantially aligned with the neutral axis when the pin is disposed in the first position. When the pin is disposed in the second position, the cantilever spring may be biased in a negative direction relative to the neutral axis.

In still another embodiment, the pin track member includes a saddle portion defined therein and positioned relative to the neutral axis such that, in the second position, the pin is retained in the saddle portion of the pin track member under the bias of the cantilever spring back toward the neutral axis.

In still yet another embodiment, the pin is configured to translate from the first position to a third position corresponding to a position proximal of the actuated position of the lever and back to the second position along the first path to retain the lever in the actuated position.

In another embodiment, the pin is configured to translate from the second position to the third position and back to the first position along the second path to return the lever to the initial position.

Another embodiment of a latch mechanism configured for use with a surgical instrument is provided. the latch mechanism includes a lever moveable relative to a housing of the surgical instrument from an initial position to an actuated position for moving an end effector assembly of the surgical instrument from a first state to a second state. A cantilever spring is engaged to the lever at a fixed end thereof and a pin is engaged to the cantilever spring at a free end of the cantilever spring. A pin track member is operably engaged to the housing of the surgical instrument. The pin track member is configured to permit translation of the pin therealong between a first position corresponding to the initial position of the lever and a second position corresponding to the actuated position of the lever. The pin is configured to translate from the first position to the second position along a first path and from the second position back to the first position along a second path different from the first path. The pin is further configured to be releasably retained in the second position upon translation of the pin from the first position to the second position along the first path.

In one embodiment, the cantilever spring is biased toward alignment with a neutral axis defined therein. In such an embodiment, the cantilever spring is capable of flexing in each of a positive direction and a negative direction relative to the neutral axis to permit translation of the pin along the first and second paths.

In another embodiment, the cantilever spring is configured to deflect in the negative direction relative to the neutral axis to permit translation of the pin from the first position to the second position along the first path. On the other hand, the cantilever spring may be configured to deflect in the positive direction relative to the neutral axis to permit translation of the pin from the second position back to the first position along the second path.

In yet another embodiment, the cantilever spring is configured to be substantially aligned with the neutral axis when the pin is disposed in the first position. When in the second position, the cantilever spring may be configured to be biased in a negative direction relative to the neutral axis.

In still another embodiment, the pin track member includes a saddle portion defined therein and positioned relative to the neutral axis such that, in the second position, the pin is retained in the saddle portion of the pin track member under the bias of the cantilever spring back toward the neutral axis.

In still yet another embodiment, the pin is configured to translate from the first position to a third position corresponding to a position proximal of the actuated position of the lever and back to the second position along the first path to retain the lever in the actuated position.

In another embodiment, the pin is configured to translate from the second position to the third position and back to the first position along the second path to return the lever to the initial position.

BRIEF DESCRIPTION OF THE DRAWINGS

Various embodiments of the presently disclosed latch mechanisms are described herein with reference to the drawings, wherein:

FIG. 7 is a perspective view of the handle assembly of the forceps of FIG. 1A wherein a portion of the housing has been removed to show the internal components therein, the handle assembly including another embodiment of a latch mechanism disposed in an actuated position;

FIG. 8 is a isolated, perspective view of a pin track member and cantilever spring of the latch mechanism of FIG. 7;

FIG. 9 is an isolated, perspective view of a lever of the latch mechanism of FIG. 7;

DETAILED DESCRIPTION

Figure 1A:
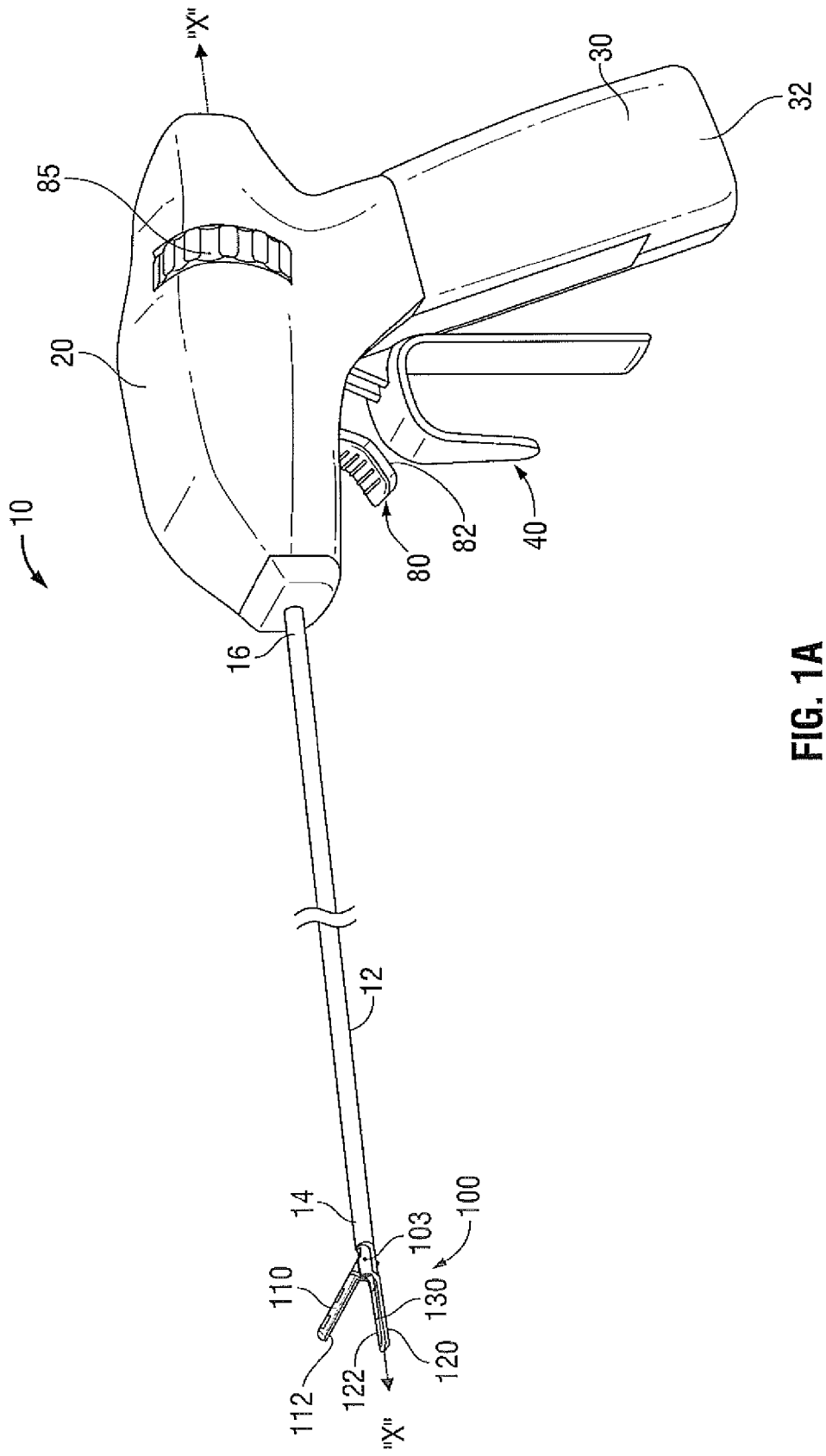
FIG. 1A is a perspective view of a forceps including an end effector assembly in accordance with an embodiment of the present disclosure wherein jaw members of the end effector assembly are disposed in a spaced-apart position.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 1B:
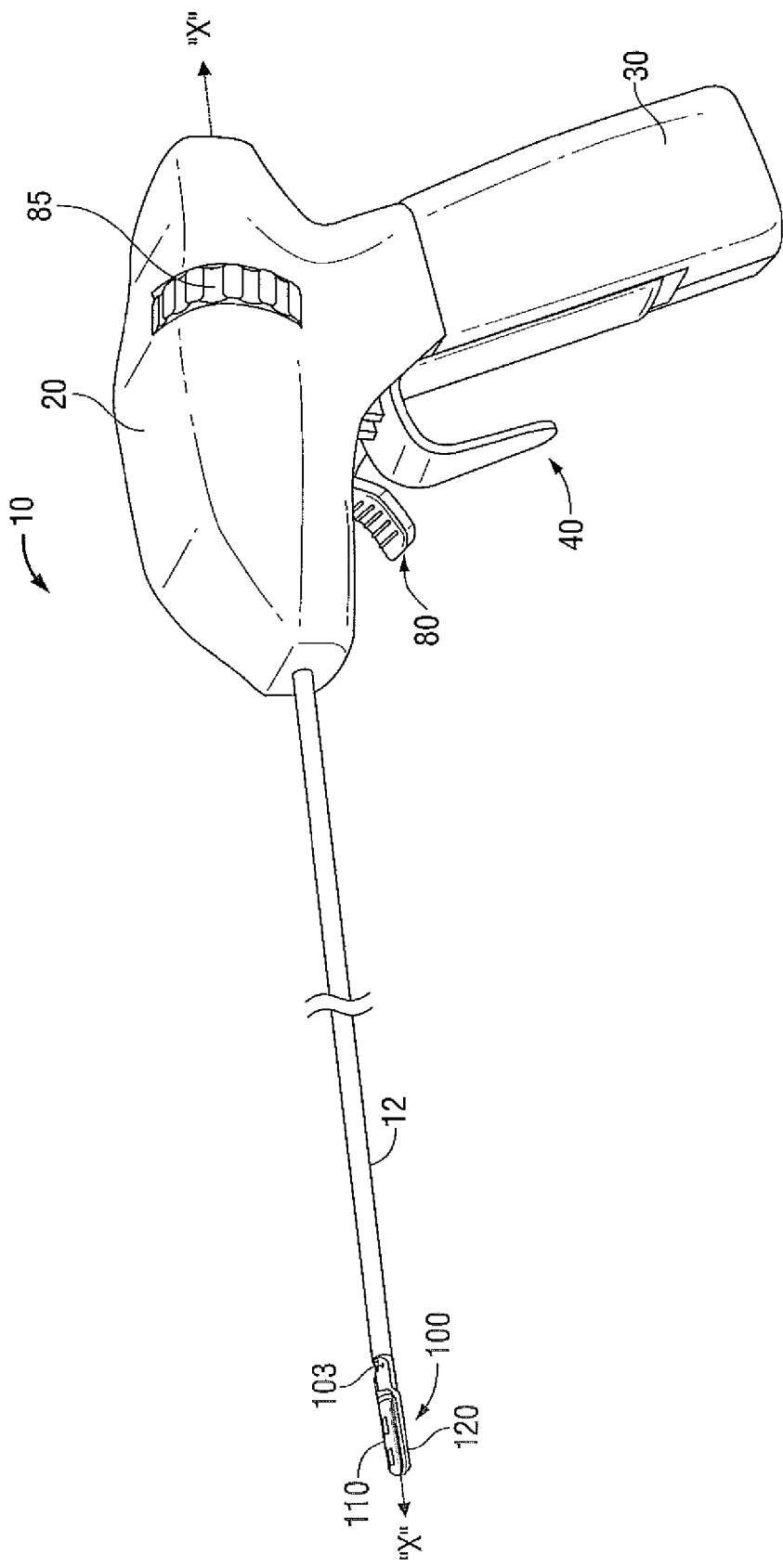
FIG. 1B is a perspective view of the forceps of FIG. 1A wherein the jaw members of the end effector assembly are disposed in an approximated position.

Turning now to FIGS. 1A and 1B, forceps 10 is one example of an instrument for use in accordance with the present disclosure. Forceps 10 including a housing 20, a handle assembly 30, a lever latch assembly 40, a trigger assembly 80, a rotating assembly 85, and an end effector assembly 100. Forceps 10 further includes a shaft 12 having a distal end 14 configured to mechanically engage end effector assembly 100 and a proximal end 16 that mechanically engages housing 20. Alternatively, any surgical instrument having a lever latch assembly operable to control one or more functions of the end effector assembly may be provided.

With continued reference to FIGS. 1A and 1B, end effector assembly 100 includes a pair of opposing jaw members 110 and 120. End effector assembly 100 is designed as a unilateral assembly, i.e., jaw member 120 is fixed relative to the shaft 12 and jaw member 110 is moveable about a pivot 103 relative to jaw member 120. However, either, or both jaw members 110, 120 may be moveable with respect to the other. In either embodiment, jaw members 110, 120 are moveable from a spaced-apart position, as shown in FIG. 1A, to an approximated position, as shown in FIG. 1B, to grasp tissue therebetween. Further, one or both of jaw members 110, 120 may include an electrically conductive tissue sealing surface 112, 122, respectively. Sealing surfaces 112, 122 are disposed in opposed relation relative to one another such that, with jaw members 110, 120 in the approximated position grasping tissue therebetween, electrosurgical energy may be supplied to one or both of sealing surfaces 112, 122 of jaw members 110, 120, respectively, to seal tissue grasped therebetween.

One or both of jaw members 110, 120 may also include a longitudinally extending blade channel 130 to permit reciprocation of a blade (not shown) therethrough for dividing tissue grasped therebetween. Trigger assembly 80 is operably coupled to the blade (not shown) such that, upon actuation of trigger 82, the blade (not shown) is translated from a retracted position to an extended position wherein the blade (not shown) is advanced between jaw members 110, 120 to cut tissue grasped therebetween. Further, trigger 82 may be biased toward an un-actuated position such that, upon release of trigger 82, the blade (not shown) is returned to the retracted position.

Rotating assembly 85 is integrally associated with housing 20 and is rotatable in either direction about a longitudinal axis "X-X" to rotate jaw members 110, 120 with respect to housing 20 about longitudinal axis "X-X."

Handle assembly 30 extends downwardly from housing 20 and is releasably engageable with housing 20. Handle assembly 30 is ergonomically configured such that, when engaged with housing 20, a surgeon may grasp handle assembly 30 and operate lever latch assembly 40, trigger assembly 80 and/or rotating assembly 85 with a single hand. Handle assembly 30 further includes a battery pack (not shown) disposed within a battery housing 32. The battery pack (not shown) of handle assembly 30 provides power to forceps 10, e.g., for energizing sealing surfaces 112, 122 of jaw members 110, 120, respectively. More particularly, the battery pack (not shown) is configured to electrically couple to a generator (not shown) disposed within housing 20 for powering the generator (not shown). The generator (not shown), in turn, supplies the desired energy to sealing surfaces 112, 122 of jaw members 110, 120, respectively, of end effector assembly 100. Alternatively, forceps 10 may be configured to be coupled to an external power source (not shown) and/or generator (not shown), e.g., via an electrosurgical cable (not shown).

Figure 2:
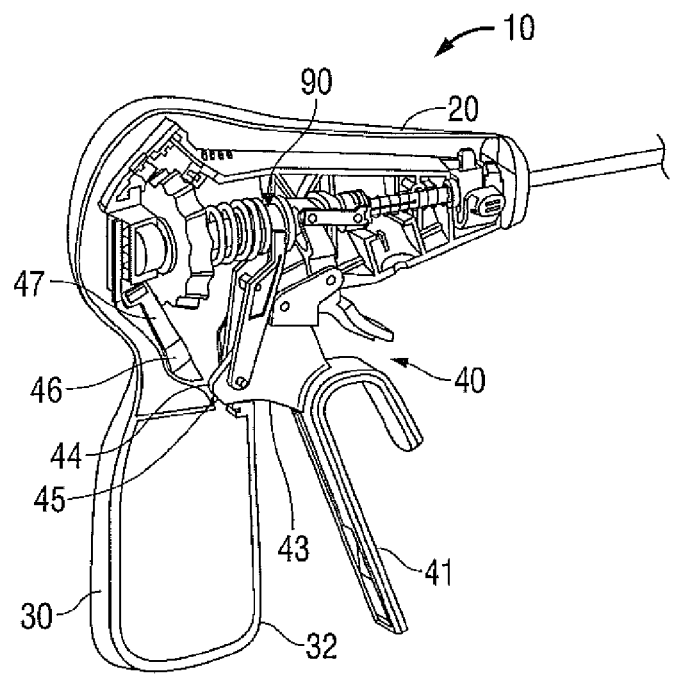
FIG. 2 is a perspective view of a handle assembly of the forceps of FIG. 1A wherein a portion of the housing has been removed to show the internal components therein, the handle assembly including a latch mechanism disposed in an initial position.
Figure 3:
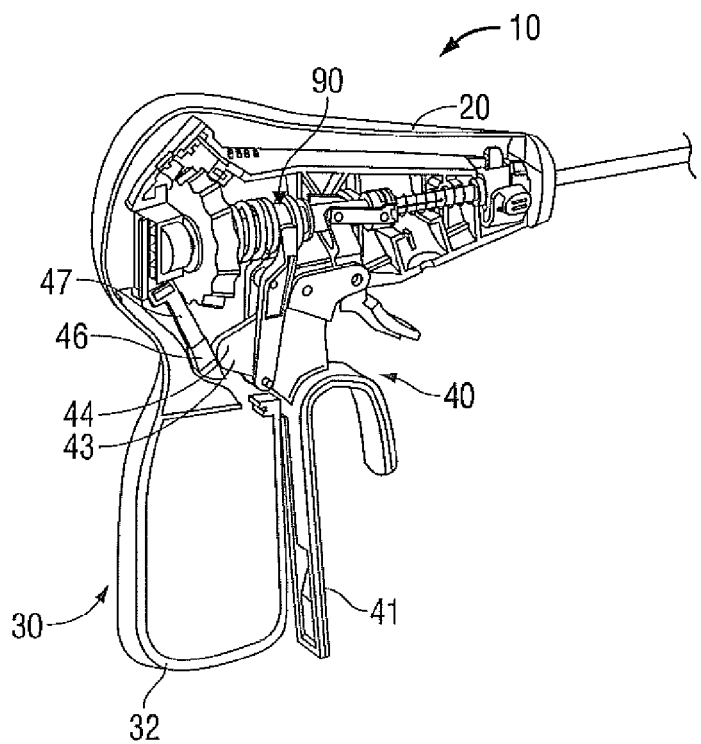
FIG. 3 is a perspective view of the handle assembly of the forceps of FIG. 1A wherein a portion of the housing has been removed to show the internal components therein and wherein the latch mechanism is disposed in an actuated position.

With reference to FIGS. 2 and 3, in conjunction with FIGS. 1A and 1B, battery housing 32 of handle assembly 30 includes mechanical keying features (not shown) configured complementarily to the mechanical keying features associated with housing 20 such that handle assembly 30 may be securely locked in mechanical engagement with housing 20. The battery pack (not shown) is electrically coupled to the generator (not shown), and may also be released from housing 20, e.g., to replace or recharge the battery pack (not shown).

Continuing with reference to FIGS. 2 and 3, one embodiment of a lever latch assembly 40 is shown including a lever 41 pivotably coupled to housing 20 and extending downwardly therefrom. Lever 41 is ultimately connected to drive assembly 90 that, together, mechanically cooperate to impart movement of jaw members 110 and 120 between the spaced-apart position (FIG. 1A) and the approximated position (FIG. 1B). As mentioned above, spatial constraints within housing 20 limit the positioning of lever 41, e.g., such that the generator (not explicitly shown) and other control circuitry (not explicitly shown) may be disposed above drive assembly 90 within housing 20. Further, as will become apparent below, the working components of lever latch assembly 40 are all relatively closely-spaced with respect to one another, thereby providing more area within housing 20 for the generator (not shown) and for engagement of the battery pack (not shown).

Continuing with reference to FIGS. 2 and 3, lever 41 is selectively moveable from an initial position (FIG. 2), wherein lever 41 is spaced-apart from handle assembly 30, to an actuated position (FIG. 3), wherein lever 41 is positioned adjacent to handle assembly 30, to move jaw members 110, 120 from the spaced-apart position (see FIG. 1A) to the approximated position (see FIG. 1B). As will be described below, lever latch assembly 40 is configured to permit movement of lever 41 between the initial position (FIG. 2) and the actuated position (FIG. 3) and for releasably locking lever 41 in the actuated position. Accordingly, lever latch assembly 40 is configured to selectively move jaw members 110, 120 (FIGS. 1A and 1B) between the spaced-apart position and the approximated position and to releasably lock jaw members 110, 120 (FIGS. 1A and 1B) in the approximated position. Further, lever 41 may be biased toward the initial position (FIG. 2), such that jaw members 110, 120 are biased toward the spaced-apart position (FIG. 1A).

Figure 4:
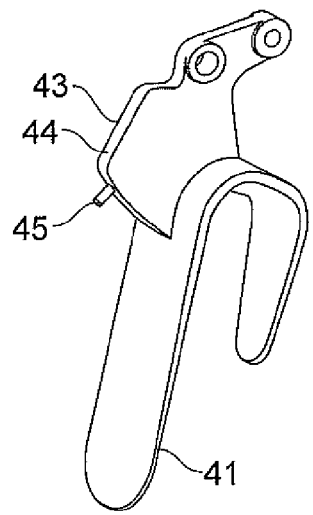
FIG. 4 is an isolated, perspective view of a lever of the latch mechanism of FIGS. 2 and 3.

Turning now to FIG. 4, in conjunction with FIGS. 2-3, lever 41 of lever latch assembly 40 includes a proximally-extending tab 43. Tab 43 extends at least partially into housing 20, e.g., through a slot (not shown) defined therein. More particularly, a proximal tip 44 of tab 43 extends into housing 20 when lever 41 is disposed in the initial position (FIG. 2), while the entire tab 43 (or a substantial portion thereof) extends into housing 20 when lever 41 is moved to the actuated position (FIG. 3). Tab 43 extends into housing 20 above handle assembly 30, as best shown in FIGS. 2 and 3, such that, when the battery pack (not shown) is engaged to housing 20, tab 43 may still be advanced into housing 20 upon movement of lever 41 from the initial position (FIG. 2) to the actuated position (FIG. 3).

A pin 45 is integrally formed with, or fixedly engaged to tab 43 of lever 41 and extends proximally therefrom. Pin 45 may be formed from a metal or other rigid material. As tab 43 is advanced into housing 20 upon movement of lever 41 from the initial position to the actuated position, pin 45 is similarly advanced into housing 20 toward pin track member 46 (FIG.

5). In other words pin 45 is translated along an arc upon movement of lever 41 between the initial position and the actuated position. However, since pin 45 is fixedly engaged within lever 41 and since lever 41 is pivotably engaged to housing 20, the transverse position of pin 45 relative to housing 20 is fixed. More specifically, pin 45 is transversely aligned with a neutral axis "N-N" (FIG. 6) defined by cantilever spring 47 throughout movement of lever 41 between the initial position and the actuated position.

Figure 5:
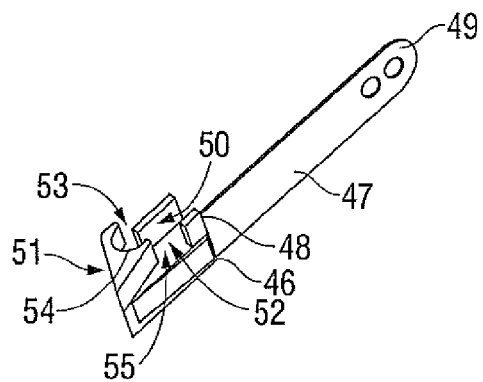
FIG. 5 is an isolated, perspective view of a pin track member and cantilever spring of the latch mechanism of FIGS. 2 and 3.
Figure 6:
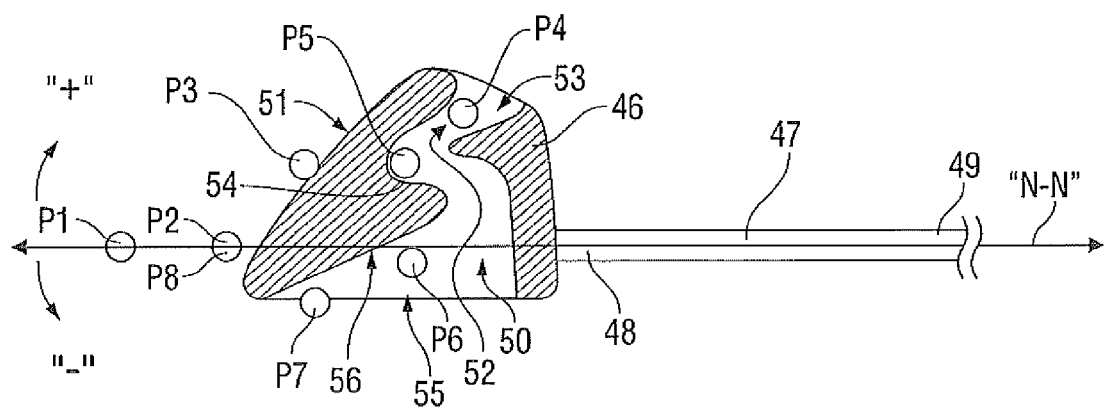
FIG. 6 is a schematic illustration of the use of the latch mechanism of FIGS. 2 and 3.

As best shown in FIG. 5, pin track member 46 defines a track 50 configured to permit translation of pin 45 therealong. Pin track member 46 is engaged, or integrally formed, e.g., insert molded, with a cantilever spring 47 at a first end 48 of cantilever spring 47. Cantilever spring 47 is coupled at a second end 49 thereof to housing 20, e.g., via protrusion-aperture friction fitting, or other suitable engagement. In other words, cantilever spring 47 is fixedly coupled to housing 20 at second end 49 thereof, while first end 48 of cantilever spring 47, having pin track member 46 disposed thereon, is free. At-rest, cantilever spring 47 is biased toward an aligned position defining the neutral axis "N-N" (FIG. 6). However, cantilever spring 47 is capable of being flexed off of the neutral axis "N-N" (FIG. 6) in both a positive direction "+" (FIG. 6) and a negative direction "−" (FIG. 6). As such, upon urging of pin track member 46 and, thus, the free first end 48 of cantilever spring 47 in either direction relative to the fixed second end 49 of cantilever spring 47, cantilever spring 47 is flexed off of the neutral axis "N-N" (FIG. 6) such that pin track member 46 is repositioned relative to the neutral axis "N-N" (FIG. 6). Under the bias of cantilever spring 47 toward an aligned position with respect to the neutral axis "N-N" (FIG. 6), pin track member 46 is likewise biased toward an aligned position with respect to the neutral axis "N-N" (FIG. 6).

Turning now to FIG. 6, in conjunction with FIGS. 2-3, the operation of lever latch assembly 40 will be described. Initially, with lever 41 disposed in the initial position (and, thus, with jaw members 110, 120 disposed in the spaced-apart position (FIG. 1A)), pin 45 extends minimally into housing 20, spaced-apart from pin track member 46. As shown in FIG. 6, this position corresponds to position $P_1$. When it is desired to close jaw members 110, 120 (FIG. 1A), e.g., for grasping tissue therebetween, the surgeon grasps handle assembly 30 and lever 41 and pulls lever 41 proximally toward handle assembly 30, i.e., toward the actuated position. As lever 41 is moved from the initial position toward the actuated position, drive assembly 90 imparts movement of jaw members 110, 120 from the spaced-apart position to the approximated position. At the same time, as lever 41 is pulled proximally, tab 43 is advanced proximally into housing 20 such that pin 45 is translated, in transverse alignment with neutral axis "N-N," toward pin track member 46 to position $P_2$. However, at this point, pin track member 46 remains aligned on the neutral axis "N-N" under the bias of cantilever spring 47.

Upon further movement of lever 41 toward the actuated position, pin 45 is advanced further proximally into housing 20, eventually contacting an outer surface 51 of pin track member 46. With pin 45 transversely fixed with respect to the neutral axis "N-N," pin 45 causes cantilever spring 47 to be flexed and urges pin track member 46 off of the neutral axis "N-N" in a negative direction "−" as pin 45 is translated through position $P_3$. More specifically, the outer surface 51 of pin track member 46 is angled relative to neutral axis "N-N" such that, as lever 41 is pulled further toward the actuated position, pin 45 is slid proximally along outer surface 51 of pin track member 46, urging pin track member 46 off of the neutral axis "N-N."

Once lever 41 has been moved to the actuated position, corresponding to the approximated position of jaw members 110, 120 (FIG. 1B), respectively, of end effector assembly 100, pin 45 has been slid proximally past angled outer surface 51 of pin track member 46 to a position $P_4$ adjacent first end 53 of track channel 52 of pin track member 46. In this position $P_4$, with pin 45 no longer contacting outer surface 51 of pin track member 46, pin 45 no longer urges pin track member 46 off of the neutral axis "N-N." As such, cantilever spring 47 is flexed back toward the aligned position, thereby moving pin track member 46 back toward alignment with the neutral axis "N-N."

When the actuated position of lever 41 has been achieved, such that jaw members 110, 120 (FIG. 1B) are disposed in the approximated position to grasp tissue therebetween, lever 41 is automatically locked in the actuated position to fix jaw members 110, 120 (FIG. 1B) in the approximated position. More particularly, once pin 45 is positioned adjacent first end 53 of track channel 52, cantilever spring 47 biases pin track member 46 back toward the neutral axis "N-N" such that pin 45 is translated along track channel 52 from position $P_4$ at the first end 53 of track channel 52 to position $P_5$ at the saddle portion 54 of track channel 52. Even if lever 41 is released at this point, pin 45 is retained in position within saddle portion 54 of track channel 52 of pin track member 46. Specifically, pin track member 46 inhibits distal translation of pin 45 and, thus lever 41, thereby maintaining jaw members 110, 120 (FIG. 1B) in the approximated position. Further, with pin 45 disposed in position $P_5$, i.e., with pin 45 disposed within saddle portion 54 of track channel 52 of pin track member 46, pin track member 46 is inhibited from returned into alignment with neutral axis "N-N."

Pin track member 46 may include one or more feedback features (not shown) for providing tactile and/or audible feedback notifying the surgeon that lever 41 has been translated to the actuated position. For example, saddle portion 54 may be configured to provide an audible or tactile response when pin 45 is translated into saddle portion 54, e.g., when pin 45 is moved to position $P_5$. Such a feature indicates to the surgeon that lever latch assembly 40 is in the locked position and that lever 41 may be released to lock jaw members 110, 120 in the approximated position.

With lever latch assembly 40 maintaining lever 41 in the actuated position and, thus, maintaining jaw members 110, 120 (FIG. 1B) in the approximated position with tissue grasped therebetween, electrosurgical energy may be supplied to sealing surfaces 112, 122 of jaw members 110, 120, respectively, to effect a tissue seal (see FIG. 1B). Thereafter, trigger 82 may be actuated to advance the blade (not shown) between jaw members 110, 120 to cut tissue along the previously formed tissue seal. Finally, lever latch assembly 40 may be unlatched, as described in further detail below, allowing lever 41 to return to the initial position and allowing jaw members 110, 120 (FIGS. 1A and 1B) to return to the spaced-apart position to release tissue such that forceps 10 may be removed from the surgical site.

In order to unlock lever latch assembly 40, lever 41 is moved further proximally from the actuated position a sufficient distance to dislodge pin 45 from saddle portion 54 of track channel 52 of pin track member 46. In other words, lever 41 is moved proximally such that pin 45 is no longer retained within saddle portion 54. Track channel 52 is configured such that, once pin 45 is removed from saddle portion 54, pin 45 enters open second end 55 of track channel 52. Once pin 45 is moved into the open second end 55 of track channel 52, e.g., once pin 45 is moved to position $P_6$, pin 45 no longer inhibits pin track member 46 from returning under the bias of cantilever spring 47 to the aligned position with respect to neutral axis "N-N." As such, cantilever spring 47 is returned to the at-rest position, thereby returning pin track member 46 into alignment with neutral axis "N-N."

At this point, with pin 45 in position $P_6$, the surgeon may release lever 41. Similarly as discussed above, pin track member 46 may include feedback features (not shown) for providing a tactile or audible indication to the surgeon that pin 45 has been removed from saddle portion 54 of track channel 52 and, thus, that lever 41 may be released allowing jaw members 110, 120 (FIGS. 1A and 1B) to return to the spaced-apart position.

Upon release of lever 41 by the surgeon, lever 41 is returned back to the initial position. As such, pin 45 is translated distally relative to pin track member 46 and housing 20. More particularly, pin 45 is translated distally from position $P_6$ along inner surface 56 of pin track member 46. Inner surface 56 of pin track member 46 is angled such that, as pin 45 is translated therealong to position $P_7$, cantilever spring 47 is flexed to permit pin track member 46 to be repositioned off of the neutral axis "N-N" in a positive direction "+." Upon further distal translation of pin 45 to position $P_8$, pin 45 exits second end 55 of track channel 52 of pin track member 46, allowing pin track member 46 to return under the bias of cantilever spring 47 back into alignment with the neutral axis "N-N." Thereafter, lever is further returned, e.g., under the bias, back to the initial position corresponding to position $P_1$ of pin 45 and corresponding to the spaced-apart position of jaw members 110, 120 of end effector assembly 100 (FIGS. 1A and 1B).

Turning now to FIGS. 7-9, another embodiment of a lever latch assembly 60 is shown configured for use with a surgical instrument, e.g., forceps 10. Similar to lever latch assembly 40 discussed above (see FIGS. 2-6), lever latch assembly 60 includes a lever 61 pivotably coupled to housing 20 and extending downwardly therefrom. Lever 61 is ultimately connected to drive assembly 90 that, together, mechanically cooperate to impart movement of jaw members 110 and 120 between the spaced-apart position (FIG. 1A) and the approximated position (FIG. 1B). More particularly, lever 61 is selectively moveable from an initial position, wherein lever 61 is spaced-apart from handle assembly 30, to an actuated position, wherein lever 61 is positioned adjacent to handle assembly 30, to move jaw members 110, 120 from the spaced-apart position (see FIG. 1A) to the approximated position (see FIG. 1B).

With continued reference to FIGS. 7-9, lever latch assembly 60 is similar to lever latch assembly 40 in that lever latch assembly 60 is configured to permit movement of lever 61 between the initial position and the actuated position and for relesably locking lever 61 in the actuated position. Accordingly, lever latch assembly 60 is configured to selectively move jaw members 110, 120 between the spaced-apart position (FIG. 1A) and the approximated position (FIG. 1B) and to releasably lock jaw members 110, 120 in the approximated position (FIG. 1B). Further, lever 61 may be biased toward the initial position, such that jaw members 110, 120 are biased toward the spaced-apart position (FIG. 1A).

Figure 11:
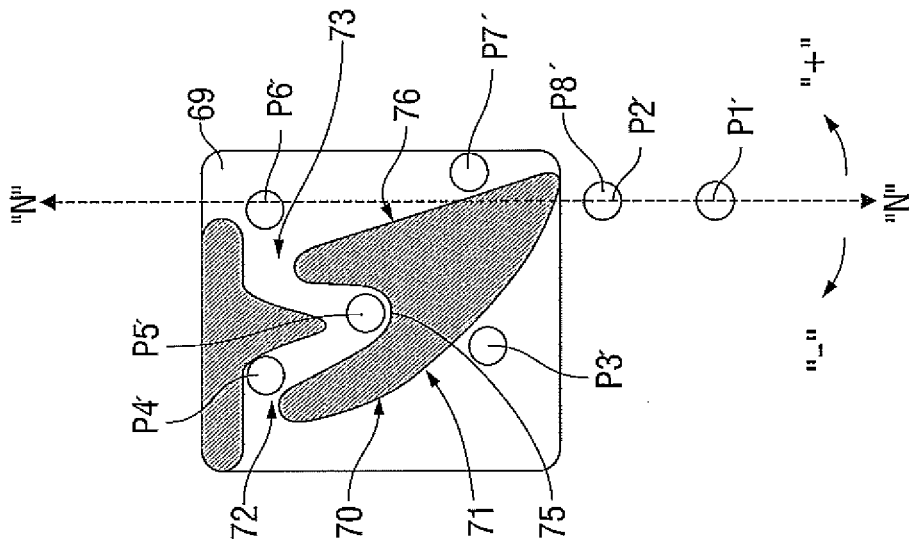
FIG. 11 is a schematic illustration of the use of the latch mechanism of FIG. 7.
Figure 10:
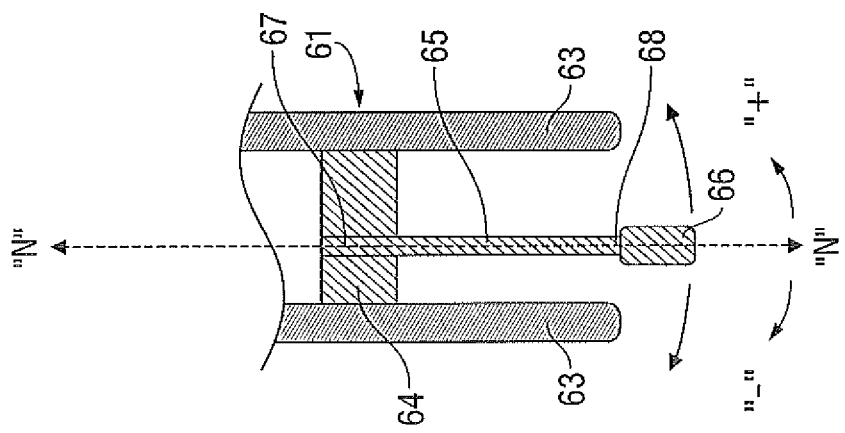
FIG. 10 is a transverse, cross-sectional view of the lever of FIG. 9.

As best shown in FIG. 9, lever 61 of lever latch assembly 60 includes a pair of flanges 63 extending upwardly therefrom. Flanges 63 extend into housing 20 to couple lever 61 to housing 20. A crossbar 64 extends between flanges 63 in a generally perpendicular orientation with respect to flanges 63. A cantilever spring 65 is fixedly engaged at a first end 67 thereof to crossbar 64 and includes a pin 66 integrally formed with, or otherwise engaged to free second end 68 of cantilever spring 65. Cantilever spring 65 extends downwardly and proximally from crossbar 64 of flanges 63 of lever 61 such that pin 66 extends generally toward housing 20. More specifically, when lever 61 is disposed in the initial position, pin 66 is spaced-apart from housing 20. On the other hand, when lever 61 is moved to the actuated position, pin 66 is positioned adjacent housing 20. Further, cantilever spring 65 is positioned off-center on crossbar 64, i.e., cantilever spring 65 is positioned asymmetrically between flanges 63 of lever 61. At-rest, cantilever spring 65 is biased toward an aligned position defining the neutral axis "N-N" (FIGS. 10 and 11). However, cantilever spring 65, similar to cantilever spring 65, is capable of being flexed off of the neutral axis "N-N" (FIGS. 10 and 11) in both a position direction "+" and a negative direction "−" to thereby reposition pin 66 off of the neutral axis "N-N" (FIGS. 10 and 11).

Referring to FIGS. 7-11, lever latch assembly 60 also includes a pin track member 69 defining a track 70 configured to permit translation of pin 66 therealong. Pin track member 69 is engaged to, or integrally formed with housing 20 in a generally distal-facing orientation and is positioned to at least partially intersect the neutral axis "N-N." As such, upon movement of lever 61 from the initial position to the actuated position, pin 66 is translated along an arc toward housing 20 and, thus, toward pin track member 69, eventually engaging pin track member 69. As will be described in greater detail below, with pin track member 69 fixedly engaged to housing 20, and with pin 66 engaged to lever 61 via cantilever spring 65, movement of lever 61 between the initial position and the actuated position causes pin track member 69 to urge the free second end 68 of cantilever spring 65 off of the neutral axis "N-N" such that pin 66 is repositioned relative to the neutral axis "N-N" to releasably lock lever 61 in the actuated position.

The operation of lever latch assembly 60 will now be described. Initially, with lever 61 disposed in the initial position (and, thus, with jaw members 110, 120 disposed in the spaced-apart position (FIG. 1A)), pin 66 is spaced-apart from pin track member 69 and, thus, cantilever spring 65 is aligned on neutral axis "N-N." As shown in FIG. 6, this position corresponds to position $P_1'$. When it is desired to close jaw members 110, 120 (FIGS. 1A-1B), e.g., for grasping tissue therebetween, the surgeon grasps handle assembly 30 and lever 61 and pulls lever 61 proximally toward handle assembly 30, i.e., toward the actuated position. As lever 61 is moved from the initial position toward the actuated position, drive assembly 90 imparts movement of jaw members 110, 120 from the spaced-apart position to the approximated position (FIG. 1B). At the same time, as lever 61 is pulled proximally, pin 66 is advanced proximally toward housing 20 such that pin 66 is translated toward pin track member 69, represented by position $P_2'$. However, at this point, pin 66 is still spaced from pin track member 69 and, thus, remains aligned on the neutral axis "N-N" under the bias of cantilever spring 65.

Upon further movement of lever 61 toward the actuated position, pin 66 is advanced further proximally toward housing 20, eventually contacting an outer surface 71 of pin track member 69. Due to the angled configuration of outer surface 71 of pin track member 69 relative to the neutral axis "N-N," and with pin track member 69 transversely fixed with respect to the neutral axis "N-N," cantilever spring 65 is flexed and pin 66 is urged of the neutral axis "N-N" in a negative direction "−" as pin 66 is translated through position $P_3'$ and along outer surface 71.

Once lever 61 has been moved to the actuated position, corresponding to the approximated position of jaw members 110, 120, respectively, of end effector assembly 100 (FIGS. 1A and 1B), pin 66 has been slid proximally past angled outer surface 71 of pin track member 69 to a position $P_4'$ adjacent first end 72 of track channel 74 of pin track member 69. In this position $P_4'$, with pin 66 no longer contacting outer surface 71 of pin track member 69, pin track member 69 no longer urges pin 66 off of the neutral axis "N-N." As such, cantilever spring 65 is flexed back toward the aligned position, thereby moving pin 66 back toward alignment with the neutral axis "N-N."

When lever is moved to the actuated position and is subsequently released, lever latch assembly 60 releasably locks lever 61 in the actuated position to fix jaw members 110, 120 in the approximated position (see FIG. 1B). More particularly, once pin 66 is positioned adjacent first end 72 of track channel 74, cantilever spring 65 biases pin 66 back toward the neutral axis "N-N" such that pin 66 is translated along track channel 74 from position $P_4'$ at the first end 72 of track channel 74 to position $P_5'$ at the saddle portion 75 of track channel 74. In this position, pin track member 69 inhibits distal translation of pin 66 and, thus lever 61, thereby maintaining jaw members 110, 120 in the approximated position. As in the previous embodiment, pin 66 and/or pin track member 69 may include one or more feedback features (not shown) for providing tactile and/or audible feedback notifying the surgeon that lever 61 has been translated to the actuated position.

With lever latch assembly 60 maintaining lever 61 in the actuated position and, thus, maintaining jaw members 110, 120 (FIG. 1B) in the approximated position with tissue grasped therebetween, electrosurgical energy may be supplied to sealing surfaces 112, 122 of jaw members 110, 120, respectively, to effect a tissue seal (see FIG. 1B). Thereafter, trigger 82 may be actuated to advance the blade (not shown) between jaw members 110, 120 (FIG. 1B) to cut tissue along the previously formed tissue seal. Finally, lever latch assembly 60 may be unlatched, as will be described in greater detail below, allowing lever 61 to return to the initial position and allowing jaw members 110, 120 (FIGS. 1A and 1B) to return to the spaced-apart position to release tissue such that forceps 10 may be removed from the surgical site.

In order to unlock lever latch assembly 60, lever 61 is moved further proximally from the actuated position a sufficient distance to dislodge pin 66 from saddle portion 75 of track channel 74 of pin track member 69. In other words, lever 61 is moved proximally such that pin 66 is no longer retained within saddle portion 75. Track channel 74 is configured such that, once pin 66 is removed from saddle portion 75, pin 66 enters open second end 73 of track channel 74. Once pin 66 is moved into the open second end 73 of track channel 74, e.g., once pin 66 is moved to position $P_6'$, pin track member 69 no longer inhibits pin 66 from returning under the bias of cantilever spring 65 to the aligned position with respect to neutral axis "N-N." As such, cantilever spring 65 is returned to the at-rest position, thereby returning pin 66 into alignment with neutral axis "N-N." At this point, with pin 66 in position $P_6'$, the surgeon may release lever 61, allowing jaw members 110, 120 to return to the spaced-apart position (see FIG. 1A). Upon release of lever 61 by the surgeon, lever 61 is returned back to the initial position. As such, pin 66 is translated distally relative to pin track member 69 and housing 20. More particularly, pin 66 is translated distally from position $P_6'$ along inner surface 76 of pin track member 69. Inner surface 76 of pin track member 69 is angled such that, as pin 66 is translated therealong to position $P_7'$, cantilever spring 65 is flexed to permit pin 66 to be repositioned off of the neutral axis "N-N" in a positive direction "+." Upon further distal translation of pin 66 to position $P_8'$, pin 66 exits second end 73 of track channel 74 of pin track member 69, allowing pin 66 to return under the bias of cantilever spring 65 back into alignment with the neutral axis "N-N." Thereafter, lever 61 is further returned, e.g., under the bias, back to the initial position corresponding to position P₁' of pin 66 and corresponding to the spaced-apart position of jaw members 110, 120 of end effector assembly 100 (FIG. 1A).

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A latch mechanism for a surgical instrument, comprising:
    a lever configured for longitudinal motion relative to a housing of the surgical instrument from an initial position to an actuated position for moving an end effector assembly of the surgical instrument from a first state to a second state;
    a pin fixed in position and extending proximally from the lever; a cantilever spring fixed to the housing of the surgical instrument at a fixed end thereof and configured to flex in a transverse direction relative to the longitudinal motion of the lever; and
    a pin track member operably engaged to the cantilever spring at a free end of the cantilever spring, the pin track member configured to permit translation of the pin therealong between a first position corresponding to the initial position of the lever and a second position corresponding to the actuated position of the lever, the pin configured to translate from the first position to the second position along a first path and from the second position back to the first position along a second path different from the first path, the pin configured to be releasably retained in the second position upon translation of the pin from the first position to the second position along the first path;
    wherein the pin is positioned in the first position outside the pin track member and in the second position inside the pin track member.

2. The latch mechanism according to claim 1, wherein the cantilever spring is biased toward alignment with a neutral axis defined therein, the cantilever spring capable of flexing in each of a positive transverse direction and a negative transverse direction relative to the neutral axis to permit translation of the pin along the first and second paths.

3. The latch mechanism according to claim 2, wherein the cantilever spring is configured to deflect in the negative transverse direction relative to the neutral axis to permit translation of the pin from the first position to the second position along the first path.

4. The latch mechanism according to claim 2, wherein the cantilever spring is configured to deflect in the positive transverse direction relative to the neutral axis to permit translation of the pin from the second position back to the first position along the second path.

5. The latch mechanism according to claim 2, wherein cantilever spring is substantially aligned with the neutral axis when the pin is disposed in the first position.

6. The latch mechanism according to claim 2, wherein the cantilever spring is biased in the negative transverse direction relative to the neutral axis when the pin is disposed in the second position.

7. The latch mechanism according to claim 6, wherein the pin track member includes a saddle portion defined therein and positioned relative to the neutral axis such that, in the second position, the pin is retained in the saddle portion of the pin track member under the bias of the cantilever spring back toward the neutral axis.

8. The latch mechanism according to claim 1, wherein the pin is configured to translate from the first position to a third position corresponding to a position proximal of the actuated position of the lever and back to the second position along the first path to retain the lever in the actuated position.

9. The latch mechanism according to claim 8, wherein the pin is configured to translate from the second position to the third position and back to the first position along the second path to return the lever to the initial position.

10. A latch mechanism for a surgical instrument, comprising:
    a lever configured for longitudinal motion relative to a housing of the surgical instrument from an initial position to an actuated position for moving an end effector assembly of the surgical instrument from a first state to a second state;
    a cantilever spring fixed to the lever at a fixed end thereof and configured to flex in a transverse direction relative to the longitudinal motion of the lever;
    a pin engaged to the cantilever spring and extending proximally from the proximal end of the cantilever spring; and
    a pin track member fixed in position to the housing of the surgical instrument, the pin track member configured to permit translation of the pin therealong between a first position corresponding to the initial position of the lever wherein the pin is spaced-apart from the pin track member and a second position corresponding to the actuated position of the lever wherein the pin is positioned adjacent to the pin track member, the pin configured to translate from the first position to the second position along a first path and from the second position back to the first position along a second path different from the first path, the pin configured to be releasably retained in the second position upon translation of the pin from the first position to the second position along the first path.

11. The latch mechanism according to claim 10, wherein the cantilever spring is biased toward alignment with a neutral axis defined therein, the cantilever spring capable of flexing in each of a positive transverse direction and a negative transverse direction relative to the neutral axis to permit translation of the pin along the first and second paths.

12. The latch mechanism according to claim 11, wherein the cantilever spring is configured to deflect in the negative transverse direction relative to the neutral axis to permit translation of the pin from the first position to the second position along the first path.

13. The latch mechanism according to claim 11, wherein the cantilever spring is configured to deflect in the positive transverse direction relative to the neutral axis to permit translation of the pin from the second position back to the first position along the second path.

14. The latch mechanism according to claim 11, wherein the cantilever spring is substantially aligned with the neutral axis when the pin is disposed in the first position.

15. The latch mechanism according to claim 11, wherein the cantilever spring is biased in the negative transverse direction relative to the neutral axis when the pin is disposed in the second position.

16. The latch mechanism according to claim 15, wherein the pin track member includes a saddle portion defined therein and positioned relative to the neutral axis such that, in the second position, the pin is retained in the saddle portion of the pin track member under the bias of the cantilever spring back toward the neutral axis.

17. The latch mechanism according to claim 10, wherein the pin is configured to translate from the first position to a third position corresponding to a position proximal of the actuated position of the lever and back to the second position along the first path to retain the lever in the actuated position.

18. The latch mechanism according to claim 17, wherein the pin is configured to translate from the second position to the third position and back to the first position along the second path to return the lever to the initial position.

* * * * *